United States Patent
Park

(10) Patent No.: US 11,344,441 B2
(45) Date of Patent: May 31, 2022

(54) THERMOPLASTIC CAST HAVING EXCELLENT DEFORMABILITY AND RIGIDITY AND PRODUCTION METHOD THEREFOR

(71) Applicants: WOORI MATERIAL INC., Daejeon (KR); Jongchil Park, Daejeon (KR)

(72) Inventor: Jongchil Park, Daejeon (KR)

(73) Assignee: WOORI MATERIAL INC., Daejeon (KR)

( * ) Notice: Subject to any disclaimer, the term of this patent is extended or adjusted under 35 U.S.C. 154(b) by 0 days.

(21) Appl. No.: 15/306,488

(22) PCT Filed: Jun. 25, 2015

(86) PCT No.: PCT/KR2015/006515
§ 371 (c)(1),
(2) Date: Oct. 24, 2016

(87) PCT Pub. No.: WO2015/199474
PCT Pub. Date: Dec. 30, 2015

(65) Prior Publication Data
US 2017/0042715 A1     Feb. 16, 2017

(30) Foreign Application Priority Data

Jun. 26, 2014 (KR) .................. 10-2014-0078562

(51) Int. Cl.
*A61F 5/058* (2006.01)
*A61F 5/01* (2006.01)
(Continued)

(52) U.S. Cl.
CPC ............ *A61F 5/0104* (2013.01); *A61F 5/058* (2013.01); *A61F 5/05825* (2013.01); *A61F 13/04* (2013.01); *B29C 45/14073* (2013.01)

(58) Field of Classification Search
CPC .... A61F 5/0104; A61F 13/04; A61F 5/05825; A61F 5/058; A61F 5/01; A61F 5/0111;
(Continued)

(56) References Cited

U.S. PATENT DOCUMENTS 4,483,332 A * 11/1984 Rind ..................... A61L 15/07
602/13
4,483,333 A * 11/1984 Wartman ............... A61F 13/04
602/7
(Continued)

FOREIGN PATENT DOCUMENTS

CN     102245703 A     11/2011
EP     0 318 788 A2     6/1989
(Continued)

OTHER PUBLICATIONS

CN Office Action in Application No. 201580034399.8 dated Aug. 14, 2018.
(Continued)

*Primary Examiner* — Keri J Nelson
(74) *Attorney, Agent, or Firm* — Maschoff Brennan

(57) ABSTRACT

A reusable thermoplastic cast may include: a core material (10) having a net shape as a result of molding a synthetic resin elastomer into a net shape by of injection molding or press-working; and a structure (20), which consists of a polycaprolactone composite material and is molded to surround the outer circumferential surface of the core material (10) by insert injection. Example embodiments improve breathability by forming a cast in a net shape and provide a cast which is structurally sturdy and appropriate for mass production by molding the cast by, e.g., insert injection.

17 Claims, 14 Drawing Sheets

(51) Int. Cl.
*B29C 45/14* (2006.01)
*A61F 13/04* (2006.01)

(58) Field of Classification Search
CPC ...... A61F 5/0118; A61F 5/04; A61F 5/05841; A61F 5/0585; A61F 5/05866; A61F 5/05875; A61F 5/00; A61F 5/05; B29C 45/14073
USPC .............................................. 600/7; 602/5–8
See application file for complete search history.

(56) References Cited

U.S. PATENT DOCUMENTS

| | | | | |
|---|---|---|---|---|
| 4,617,921 A | * | 10/1986 | Seeler | A61F 13/04 602/7 |
| 5,718,674 A | | 2/1998 | Penrose | |
| 6,074,354 A | | 6/2000 | Scholz et al. | |
| 6,942,628 B1 | | 9/2005 | Watson | |
| 2006/0004313 A1 | * | 1/2006 | Heinz | A61F 5/01 602/7 |
| 2007/0004993 A1 | * | 1/2007 | Coppens | A61F 5/0104 602/7 |
| 2008/0154164 A1 | * | 6/2008 | Sheehan | A61F 5/01 602/7 |
| 2010/0036300 A1 | * | 2/2010 | Sheehan | A61F 5/05825 602/7 |
| 2011/0224385 A1 | * | 9/2011 | Shoji | C07D 273/08 525/437 |
| 2012/0004587 A1 | * | 1/2012 | Nickel | A61F 5/0118 602/21 |
| 2014/0039366 A1 | * | 2/2014 | Joseph | A61F 5/05825 602/7 |
| 2015/0282975 A1 | * | 10/2015 | Herzman | A61F 5/05 602/6 |

FOREIGN PATENT DOCUMENTS

| | | |
|---|---|---|
| EP | 2 537 882 A1 | 12/2012 |
| JP | S57-126843 A | 8/1982 |
| JP | H01-201361 A | 8/1989 |
| JP | H08-508909 A | 9/1996 |
| JP | H09-504454 A | 5/1997 |
| JP | 3051373 U | 6/1998 |
| JP | 3051373 U | 8/1998 |
| KR | 10-0385792 B1 | 6/2003 |
| KR | 10-2012-0086134 A | 8/2012 |
| KR | 10-2014-0070824 A | 6/2014 |
| WO | 2006/027763 A2 | 3/2006 |
| WO | 2008/041215 A1 | 4/2008 |
| WO | 2014/084425 A1 | 6/2014 |

OTHER PUBLICATIONS

CN Office Action in Application No. 201580034399.8 dated Jun. 3, 2019.
CN Office Action in Application No. 201580034399.8 dated Mar. 16, 2020.
EP Search Report in Application No. 15811239.1 dated Mar. 1, 2018.
JP Office Action in Application No. 2017-512622 dated Oct. 17, 2017.

* cited by examiner

THERMOPLASTIC CAST HAVING EXCELLENT DEFORMABILITY AND RIGIDITY AND PRODUCTION METHOD THEREFOR

TECHNICAL FIELD

The present invention relates to a thermoplastic cast having excellent deformability and rigidity and a production method therefor, and more particularly, a thermoplastic cast which prevents a fractured or injury part (an affected part) of an arm or a leg or a body of a human being or an animal from being moved while receiving treatment at an orthopedic office or the like, has excellent deformability to be easily treated when being attached to the affected part and enables mass production, and a production method therefor.

BACKGROUND ART

Generally, when a joint, an arm, a leg or a spine is fractured or injured, the injured joint, arm, leg or spine is fixed using a cast, a plaster cast, a splinter, an orthopedic appliance (a brace) or the like (hereinafter, referred to as a "cast") to be smoothly treated at an orthopedic office or the like.

In the related art, the cast is generally provided at an affected part to fix the injured joint, arm, leg or spine using a bondage and gypsum. However, the gypsum has some disadvantages that it is heavy and may not be remolded after coagulating, it is also hard for a patient to take a bath or a shower because it is deteriorated or damaged when being exposed to moisture and a part at which the cast is provided is not easily aerated.

For this reason, recently there has been developed a cast having a structure which is not damaged due to the bath or the shower and is also easily aerated. As an example thereof, there is a cast disclosed in U.S. Pat. No. 6,673,029. As illustrated in FIGS. 1a and 1b, the cast is formed in a net shape having a large-sized mesh 120. At this point, a material forming the net shape is formed by stacking a fiber-glass fiber 110, which is impregnated with a resin to have a sufficient strength to sturdily support and protect a body part, in 6 to 12 layers to form a plate board and then cutting the plate board so that meshes thereof are formed to have a hexagonal mesh arrangement. In the cast 100 (a reticulate body), it is difficult to stack the resin-impregnated fiber-glass fiber 110 in multiple layers. Also, when the resin-impregnated fiber-glass fiber 110 is stacked in multiple layers, a surface of a fiber layer is not smooth due to an uneven impregnation in a resin impregnation process, and when the cast 100 having the non-smooth surface is provided, a patient may feel uncomfortable. Therefore, since a separate layer should be formed again at a portion thereof which is in contact with the patient's skin to form a smooth surface, a manufacturing process becomes complicated.

And even when the separate layer is formed at a surface thereof which is in contact with the patient's skin, a surface of a layer located at an inside thereof may not be smooth, and thus a portion thereof stacked thereon may not be smooth. Therefore, when a layer which is in contact with the patient's skin is not formed to have a predetermined thickness or more, the patient may still feel uncomfortable.

Furthermore, in the above-described patent document, to manufacture the cast 100 in the form of the reticulate body, first, a cloth is prepared using the fiber-glass fiber 110 and then cut in a diamond shape to form the mesh. Accordingly, a ply of the fiber-glass fiber 110 may be released from a cut portion thereof. In this case, strength of the cast 100 may be weakened. Also, when a portion of the released ply is impregnated with a resin, the portion may be acuminated and may irritate the patient's skin.

In addition, since the cast 100 is manufactured by being impregnated with a water curable resin, contact with water or moisture should be prevented in the manufacturing process, and the manufacturing process should be performed in a hermetically sealed space from which moisture or humidity is removed, and thus productivity is lowered, and also since the cast 100 should be prevented from being in contact with the moisture even after being manufactured, the manufactured cast should be stored in a sealed state and thus a manufacturing arrangement is difficult and a cost is increased in manufacturing and management thereof. Also, when the cast 100 is cured, it may not be used again. Therefore, even when it is necessary to modify the cast 100 according to a degree of a patient's restoration, it is difficult to modify and reuse the cast 100.

To solve the above-described problems of the water curable cast, there has been developed a cast formed of a thermoplastic reticulate body. As an example thereof, there is a thermoplastic cast disclosed in U.S. Patent Publication No. 2008-0154164.

As illustrated in FIGS. 2a and 2b, in the cast disclosed in U.S. Patent Publication No. 2008-0154164, a splint member 210 of the cast 200 is formed in a net shape having an approximately diamond-shaped opening so that a plurality of diamond-shaped passages 220 are formed therebetween. A material in which an additive such as lignocellulose is mixed with a base material formed of a polycaprolactone composite material which may be cold-molded to have a sufficient strength to sturdily support and protect a body part may be used as a material of the splint member 210. Due to such a structure and material, while stretching in a lengthwise direction of a side thereof is limited, it may be easily stretched in a direction in parallel with an axial line 1 and an axial line 3 so that a diamond shape of the reticulate body may be easily deformed according to an appearance of a body (hereinafter, this is referred to as a 'deformation' and distinguished from the 'stretching' in which a length of the side is stretched) and thus a medical procedure is easily performed.

However, the cast disclosed in the above-described patent document may be deformed to be relatively easily applied to a patient's body, but since an entire cross section of the splint member 210 of the net shape is molded with a polycaprolactone composite material in which lignocellulose is added, there is a disadvantage that the strength thereof is weak. Also, due to such weakness of the material, the stretching in the lengthwise direction of a side is not limited but is performed slightly. In this case, a thickness of the side is reduced, and thus the strength of the cast may be weakened, and there is another disadvantage that it is difficult to maintain an original shape.

Meanwhile, when the cast formed of the above-described material is used, first, an underlying padding or a skin protection pad formed in the net shape having a relatively small-sized mesh is provided around the affected part to protect the patient's skin, and then the cast formed in the net shape having a relatively large-sized mesh is molded at an upper portion of the underlying padding by heating to surround the affected part while maintaining plasticity and then fixed by a clip or the like. As described above, when the underlying padding is provided at a lower portion of the cast, ventilation is not smoothly performed, and also when water permeates through the underlying padding due to a shower or the like, the water may be remained for a long time at the underlying padding, and thus the user may feel uncomfortable.

Further, when the underlying padding is additionally provided at the lower portion of the cast, the underlying padding may not be freely moved but may be pushed, and thus the user may also feel uncomfortable. Also, a use period of the underlying padding is shorter than that of the cast, and thus when it is necessary to replace the underlying padding, the cast should be melted by applying heat, and then the cast should be molded again after replacing the underlying padding. Therefore, there is another problem that a replacing process is difficult and inconvenient.

Therefore, it is required to develop a cast having a structure in which the strength thereof may be maintained by limiting the stretching in the lengthwise direction of the side when the cast is applied to a patient's body part and the cast may be easily applied by allowing the diamond-shaped mesh to be easily deformed according to the appearance of the patient's body part and also the patient does not feel uncomfortable.

SUMMARY

In an example embodiment, a thermoplastic cast configured to cover and fix a fractured part of a patient's body includes a structure configured to cover at least a part of the fractured part of the patient and an outer cover that covers the structure. The structure includes a thermoplastic resin configured to be deformed to conform to the part of the fractured part by heating. The structure is formed as a net shaped body with holes. The structure and the outer cover are configured to be deformed to conform to the part of the fractured part thanks to the holes. The thermoplastic cast includes multiple elongate portions connected together and crossing each other. A cross-section of each of the elongate portions in a plane orthogonal to a length of the corresponding elongate portion includes the structure surrounded by the outer cover. A first elongate portion of the elongate portions includes a groove that is recessed inward in a first direction orthogonal to a length of the first elongate portion. In a cross-section of the first elongate portion in a plane orthogonal to a length of the first elongate portion and that passes through the groove, a thickness of the first elongate portion is thinner at the groove than to either side of the groove. The groove is recessed inward in the first elongate portion at an intersection of the first elongate portion with a second elongate portion of the elongate portions of the structure.

In another example embodiment, a thermoplastic cast configured to cover and fix a fractured part of a patient's body includes a net-shaped reticulate body including multiple elongate portions. The elongate portions include a first subset of elongate portions and a second subset of elongate portions. The first subset of elongate portions are arranged parallel to each other and the second subset of elongate portions are arranged parallel to each other. The first subset of elongate portions are not parallel to the second subset of elongate portions. Each of the first subset of elongate portions intersects some of the second subset of elongate portions. Each of the second subset of elongate portions intersects some of the first subset of elongate portions. Each of the elongate portions includes a cross-section orthogonal to a length of a corresponding elongate portion that includes a core surrounded by an intermediate layer and the intermediate layer surrounded by an outer cover. A specific elongate portion of the elongate portions includes a recess that extends from a bottom of the specific elongate portion inward toward the core. In a cross-section of the specific elongate portion orthogonal to the length of the specific elongate portion and through the recess, the cross-section of the specific elongate portion: has a first thickness at the recess through the outer cover, the intermediate layer, and the core; and has a second thickness to either side of the recess exclusively through the outer cover and the intermediate layer. The first thickness at the recess through the outer cover, the intermediate layer, and the core is less than the second thickness to either side of the recess exclusively through the outer cover and the intermediate layer.

In another example embodiment, a thermoplastic cast is configured to cover and fix a fractured part of a patient's body and includes a structure configured to cover at least a part of the fractured part of the patient and an outer cover that covers the structure. The structure includes a thermoplastic resin configured to be deformed to conform to the part of the fractured part by heating. The structure is formed as a net shaped body with holes. The structure and the outer cover are configured to be deformed to conform to the part of the fractured part thanks to the holes. The thermoplastic cast includes multiple elongate portions connected together and crossing each other. A cross-section of each of the elongate portions in a plane orthogonal to a length of the corresponding elongate portion includes the structure surrounded by the outer cover. A first elongate portion of the elongate portions includes a groove that is recessed inward in a first direction orthogonal to a length of the first elongate portion. In a cross-section of the first elongate portion in a plane orthogonal to a length of the first elongate portion and that passes through the groove, a thickness of the first elongate portion is thinner at the groove than to either side of the groove. The thermoplastic cast further includes a core material having a net shape by molding a synthetic resin elastomer into the net shape by injection molding or press-working. The structure surrounds the core material. The core material has a first melting point and the structure has a second melting point that is lower than the first melting point of the core material.

DISCLOSURE

Technical Problem

The present invention is directed to providing a thermoplastic cast having excellent deformability and rigidity, which has a sufficient strength as well as the deformability and allows a user not to feel uncomfortable when being applied to the user, and a production method therefor.

Technical Solution

One aspect of the present invention provides a thermoplastic cast which has excellent deformability and rigidity, including a core material having a net shape by molding a synthetic resin elastomer into the net shape by injection molding or press-working; and a structure formed of a polycaprolactone composite material and molded to surround an outer circumferential surface of the core material by insert injection.

Another aspect of the present invention provides a production method for a thermoplastic cast which has excellent deformability and rigidity, wherein the cast includes a core material having a net shape and formed of a synthetic resin elastomer; and a structure formed of a polycaprolactone composite material to surround an outer circumferential surface of the core material, and the core material is manufactured by a reticulate body molding operation in which a net-shaped reticulate body is formed by molding a synthetic resin into a net shape by injection molding or press-working, and the structure is manufactured by a core material seating operation in which the core material is seated inside a mold for manufacturing a structure and a structure molding operation in which the structure is molded by injecting a polycaprolactone composite material to an outer circumferential surface of the core material seated inside the mold for manufacturing a structure.

In the core material seating operation, a guide cap may be installed above the mold for manufacturing a structure, and the core material may be seated inside the mold for manufacturing a structure by moving down a pressing member while the core material is put on the guide cap.

The production method may further include an outer cover molding operation in which an outer cover formed of a rubber material is molded and attached to an outside of the structure by insert injection after the structure molding operation.

In the outer cover molding operation, one or more grooves each of which has an inclined surface may be formed at a part of a lower surface of the structure, and movable insertion spacers which are formed in shapes corresponding to the grooves having the inclined surface and inserted into the one or more grooves may be provided at a mold for manufacturing an outer cover which molds the outer cover.

Movable support spacers may be provided at the mold for manufacturing an outer cover in a direction opposite to the movable insertion spacers.

In the outer cover molding operation, movable support spacers may be provided at the mold for manufacturing an outer cover, and the structure may be located at an internal center of the mold for manufacturing an outer cover, and thus the outer cover may be molded to have a predetermined thickness.

At this point, an outer cover formed of a rubber material may be molded and attached to an outside of the structure by the insert injection.

Polyethylene (PE), polyurethane (PU) or polybutene (PB) may be added to the polycaprolactone composite material forming the structure.

One of talc, sorbitol, or sodium benzoate as a nucleating agent may be added to the polycaprolactone composite material forming the structure.

A groove which is recessed inward may be formed at a portion at which the structures cross each other.

Advantageous Effects

Since the cast according to the present invention is formed in the net shape, it has excellent breathability, and also since the cast is manufactured using thermoplastic polycaprolactone having a lower melting point as a main material and thus can be easily deformed by heating in hot water or the like, an applicable patient's body part is not limited and also the cast can be easily applied.

Also, since the cast of the present invention is light and also thinner than a conventional cast formed of polyurethane and thus allows a patient to wear clothes on the applied cast, it is easy to use the cast and also to freely move.

Further, since the structure forming a surface of the cast of the present invention is molded by the insert injection, the surface of the cast is smooth, and thus the patient does not feel uncomfortable when the cast is in contact with the patient's skin. Also since the core material and the structure are molded by a mechanical method, automation and mass production can be enabled.

And since the structure of the cast of the present invention is formed of a thermoplastic resin, a hermetically sealed space for cutting off moisture or the like is not required. If necessary, the cast can be easily modified by reheating and can also be used repeatedly.

Also, since the core material is provided inside the structure formed of the polycaprolactone composite material and an outside thereof is surrounded by the outer cover, the structure can be restricted by them from being excessively stretched when being heated and then applied and can also sturdily support the body part due to appropriate elasticity.

And since the structure of the present invention is formed of the polycaprolactone composite material in which fiber-reinforced glass fiber, carbon fiber or polyethylene terephthalate fiber is added to polycaprolactone, it has excellent flexure strength and impact strength and thus can sturdily support a fractured part or the like.

In addition, since the outer cover of a hypoallergenic rubber material is provided at the cast of the present invention, a chemical component forming the cast can be prevented from being in direct contact with the patient's skin, and also a buffer effect can be expected. Therefore, it is not necessary to previously provide a skin protection pad or the like at a lower portion of the cast to protect the skin.

Furthermore, the outer circumferential surface of the structure is filled with a material of the outer cover by injection while the structure is spaced apart from a mold for manufacturing an outer cover at a predetermined distance by a movable spacer so that the outer cover having a predetermined thickness or more is molded, and thus the outer cover is hardly damaged even when the cast is used for a long time, and the structure is not exposed to an outside of the outer cover.

| <Detailed Description of Main Elements> | |
|---|---|
| 1: cast | 2: mold for manufacturing a structure |
| 3: a mold for manufacturing outer cover | 2A: groove |
| 2B: guide cap | 2C: pressing member |
| 2D: spacer | 2E: protrusion |
| 3A: molding groove | 3B: movable insertion spacer |
| 3C: movable support spacer | 3D, 3E, 3F and 3G: movable support spacer |
| 10: core material | 20: structure |
| 21: groove | 30: outer cover |
| F: fixing member | |

MODES OF THE INVENTION

Hereinafter, a configuration and an operation of the present invention will be described in detail with reference to the accompanying drawings illustrating an exemplary embodiment.

The present invention relates to a cast which is used to surround and fix or correct a patient's fractured part or the like. As illustrated in FIGS. 3 to 8, the cast according to the present invention includes a core material 10, a structure 20 which surrounds outside the core material 10, and an outer cover 30 which is formed to surround outside the structure 20.

The core material 10 is formed of a thermoplastic synthetic resin elastomer, and an entire appearance thereof is formed in a net shape in which openings having a predetermined shape are regularly formed at an inside thereof. The core material 10 is manufactured by injection molding or press-working. At this point, the synthetic resin elastomer forming the core material 10 has a melting point which is higher than that of the structure 20 and is manufactured with the synthetic resin elastomer used as a base material of the structure 20, e.g., PU, PE, soft PVC, PP copolymer or the like.

And the core material 10 is located inside the structure 20 while being formed of an elastic material, such as PU, PE, soft PVC and PP copolymer, which has the melting point which is higher than that of the structure 20 and thus has a relatively small plastic deformation due to heat. Therefore, it is possible to solve the following problems. When the cast of the present invention is deformed by applying heat and an external force to be provided at a patient's affected part, the structure 20 formed of a polycaprolactone composite material which will be described later may be excessively stretched, and in this case, a thickness of the structure becomes thinner, and a flexural strength thereof is also weakened, and also the difficulty in maintaining an appearance thereof according to an appearance of a patient's treatment area may be complemented. As a result, even when the external force is applied to the cast for a medical procedure, a shape deformation of the cast occurs, but stretching in a lengthwise direction thereof hardly occurs. Accordingly, a lengthwise deformation of a mesh of the cast formed in the net shape hardly occurs, and a thickness of a side thereof does not become thinner but is maintained.

Figure 1A:
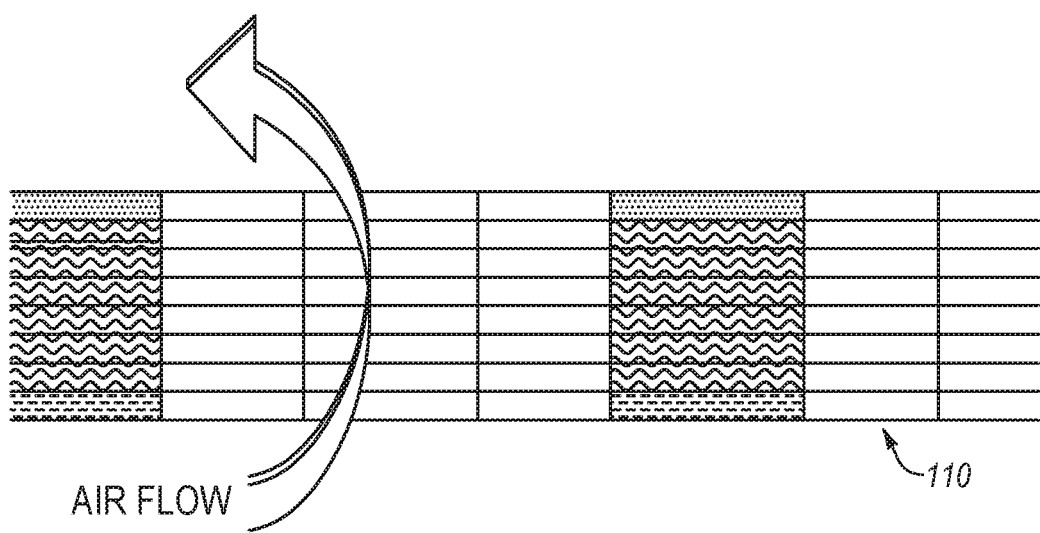
FIGS. 1a and 1b are views illustrating an example of a cast according to the related art.
Figure 1B:
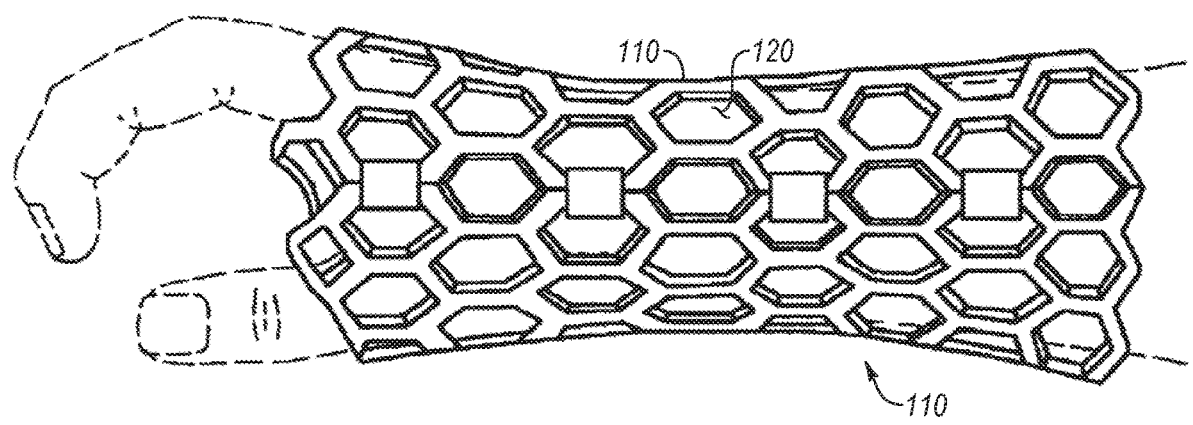
Figure 2A:
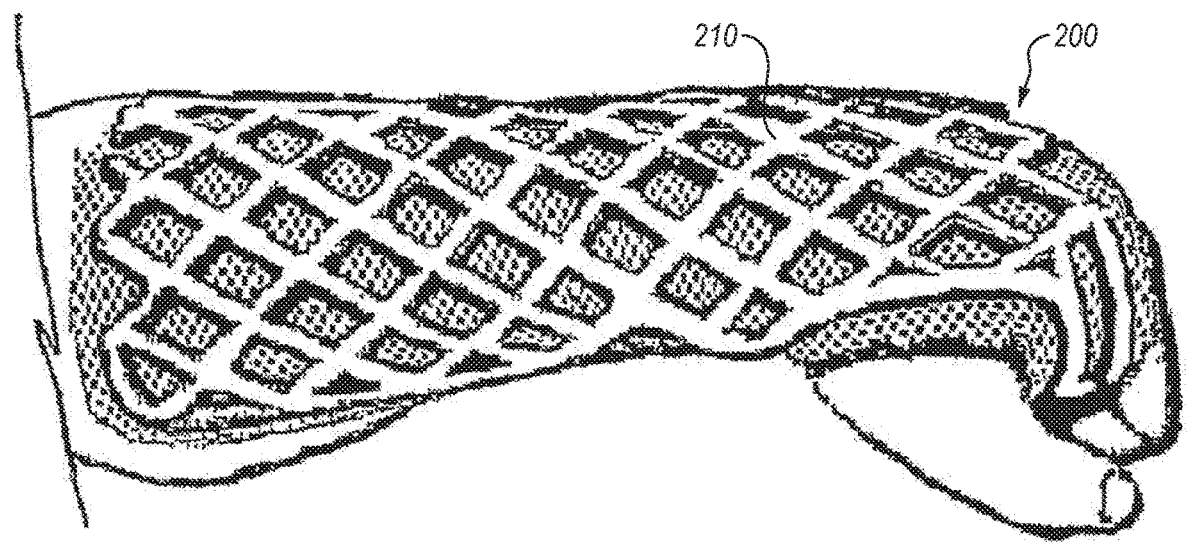
FIGS. 2a and 2b are views illustrating another example of the cast according to the related art.
Figure 2B:
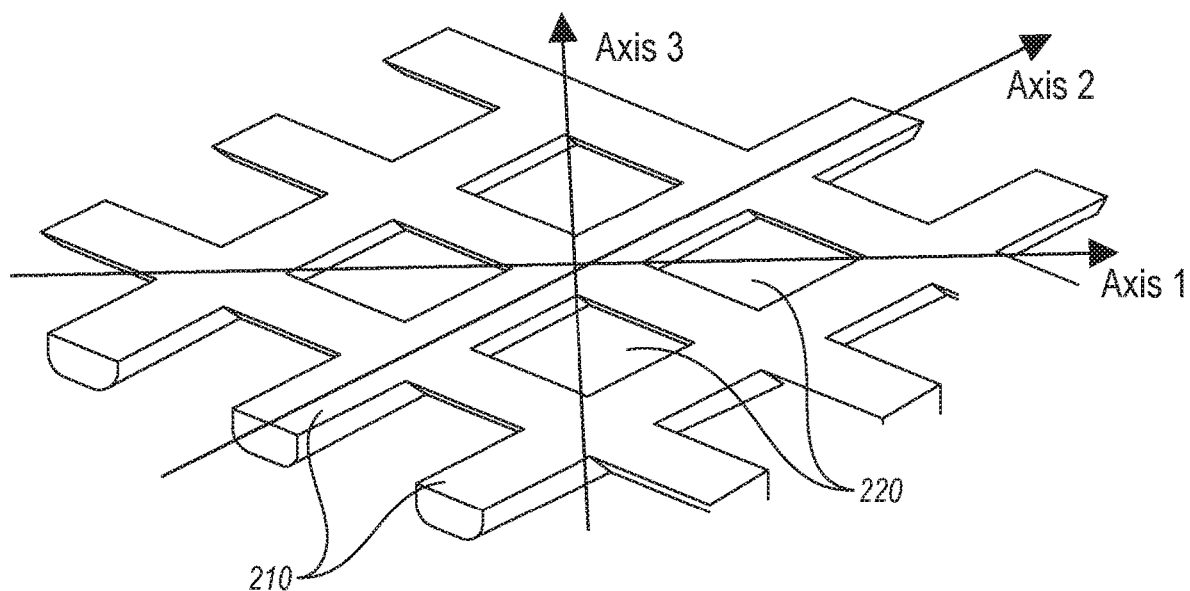
Figure 3:
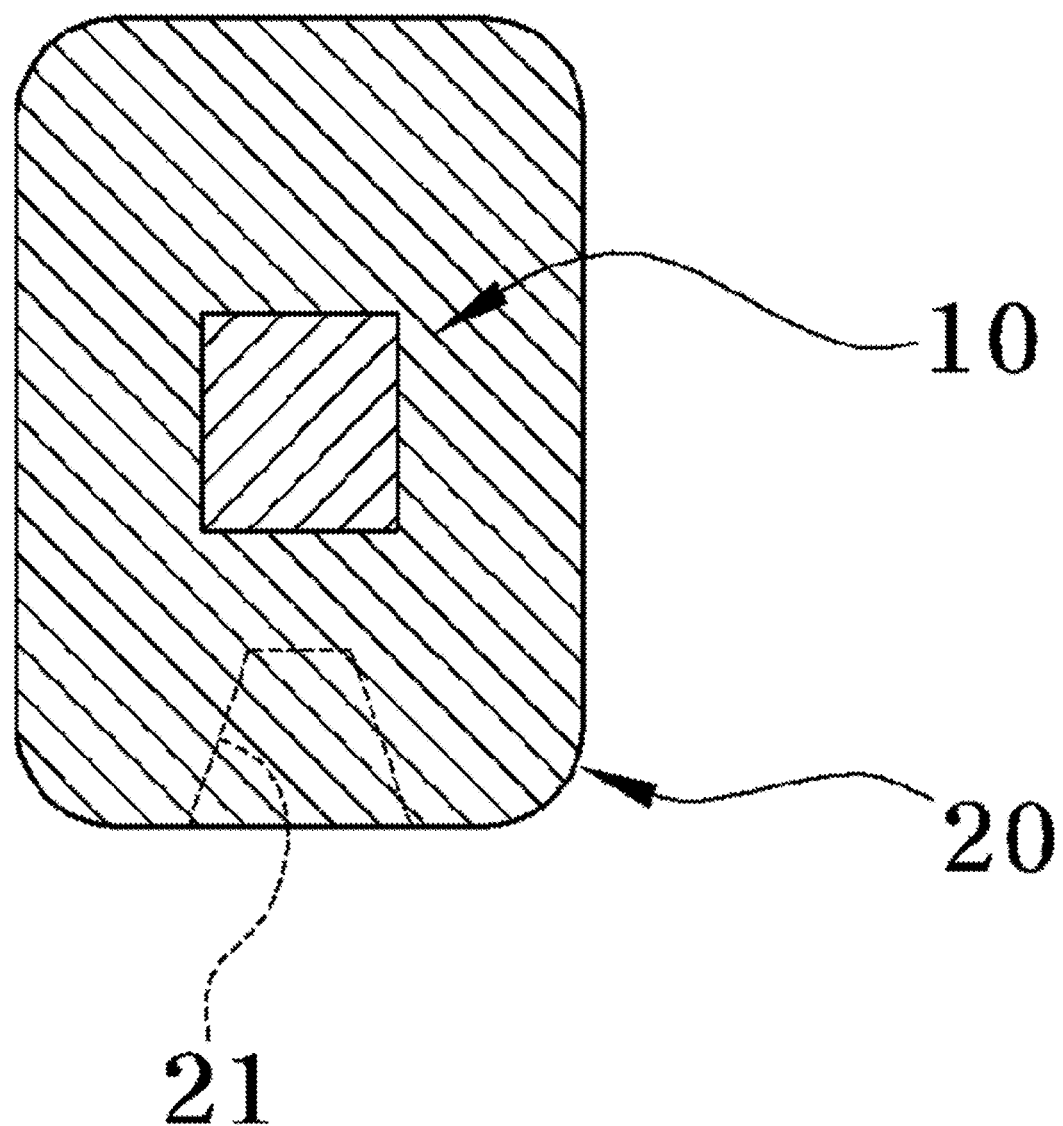
FIG. 3 is a cross-sectional view illustrating an example in which a structure is molded at an outer circumferential surface of a core material of a thermoplastic cast according to the present invention.

As illustrated in FIG. 3, the structure 20 is formed at an outer circumferential surface of the core material 10 to surround outside the core material 10. At this point, the structure 20 is formed of the polycaprolactone composite material which uses polycaprolactone as a main material, and each of the sides of the structures 20 is formed to have a quadrangular cross section shape in which a height thereof is relatively larger than a width thereof. Therefore, sufficient rigidity with respect to an external force or an impact is ensured.

And as described above, the structure 20 is formed of the polycaprolactone composite material. The polycaprolactone composite material includes polycaprolactone as the main material and a reinforcing agent formed of fiber-reinforced glass fiber or polyethylene terephthalate fiber. Due to such an additive, the strength of the structure 20 is enhanced. Therefore, a width of the structure 20 may be reduced, and a proportion of a diamond-shaped breather is increased, and thus breathability of the cast may be enhanced, and a weight thereof may also be reduced.

Also, polyethylene (PE), polyurethane (PU) or polybutene (PB) may also be added as an additive for the structure 20. Since these additives may reduce a material cost of the structure 20 and may also control a curing time thereof, it is possible to sufficiently ensure a time for applying the cast to the affected part.

In the present invention, as described above, since the melting point of the core material 10 is higher than that of the structure 20, even when the cast is heated to be applied to the affected part and the structure 20 surrounding the outside of the core material 10 is melted and softened, the core material 10 formed of the elastomer having the high melting point restricts the stretching in the lengthwise direction, and thus a length of the cast is constantly maintained although a shape thereof is deformed, and the cast may be easily applied to a peripheral portion of the affected part. Also, since the core material 10 and the structure 20 are formed of materials which are friendly to each other, the core material 10 and the structure 20 molded and attached to the outer circumferential surface of the core material 10 may be firmly coupled to each other. As a result, separation or delamination due to a difference in the materials between the core material 10 and the structure 20 may be prevented.

The outer cover 30 may be attached to an outer circumferential surface of the structure 20 by molding. The outer cover 30 is molded with a rubber material by insert injection.

Since the main material of the structure is the thermoplastic resin having a low melting point of 60 to 70° C. and a melting point of each of the core material and the outer cover is generally 100° C. or more, when the cast is heated to 70 to 100° C. using a water bath or the like, the structure may be melted and thus may be deformable, and since the core material and the outer cover are not melted but are formed of the elastic materials, the cast including the core material, the structure and the outer cover may be deformed. When the cast is deformed, the cast is prevented by a role of the core material and a subsidiary role of the outer cover from being excessively stretched.

Therefore, the length of the mesh of the cast formed in the net shape is not changed greatly. As a result, the thickness of the side does not become thinner, and thus flexure strength and impact strength of the cast are maintained as they are.

And when the cast is applied according to a shape of the patient's affected part and then cooled so that a temperature thereof is reduced, the structure is crystallized and solidified to be hard, and the outer cover serves as a skin protection pad which is comfortably applied to the skin due to elasticity.

Figure 4:
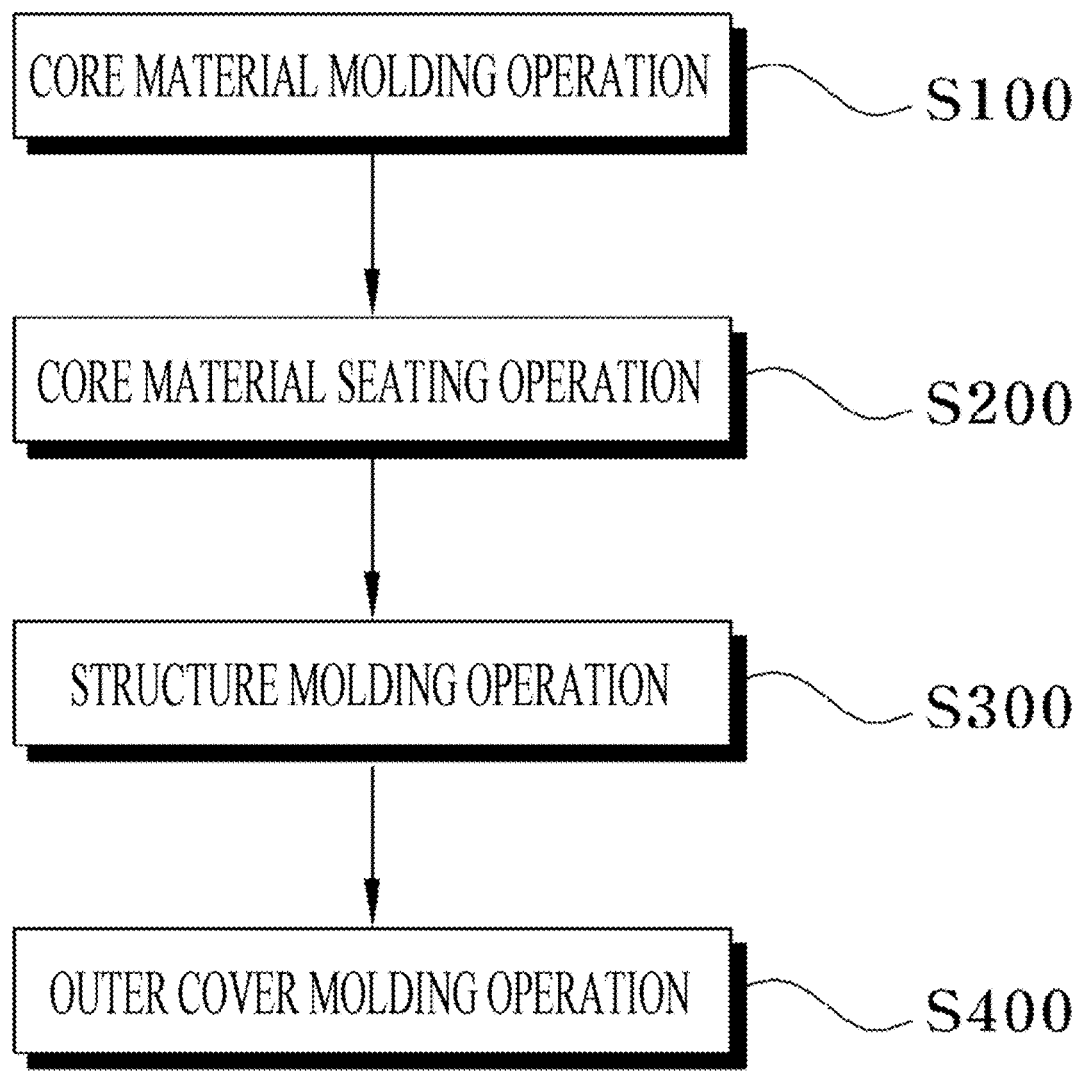
FIG. 4 is a flowchart sequentially illustrating a production method for the cast according to the present invention.

As illustrated in FIG. 4, the cast 1 of the present invention having the above-described configuration is manufactured through a core material molding operation S100, a core material seating operation S200, a structure molding operation S300 and an outer cover molding operation S400. Hereinafter, each of the operations will be described.

(1) Core Material Molding Operation (S100)

In this operation, the core material in the form of a net-shaped reticulate body is molded by regularly forming openings having constant sizes and shapes by injection molding or press-working. At this point, the material forming the core material 10 is formed of the synthetic resin elastomer, such as PU, PE, soft PVC and PP copolymer, which has the higher melting point than that of the polycaprolactone composite material forming the structure 20. This allows the core material 10 to maintain an initially molded shape even at a room temperature, and thus in the core material seating operation which will be described, the core material 10 is allowed to be easily seated inside a mold 2 for manufacturing a structure, and thus mass production may be enabled.

And a cross section shape of the side of the core material 10 formed in the net shape is formed in a rectangular shape or a square shape, and a width and a height thereof may have ranges of 1 to 3 mm and 2 to 4 mm, respectively.

(2) Core Material Seating Operation (S200)

Figure 5A:
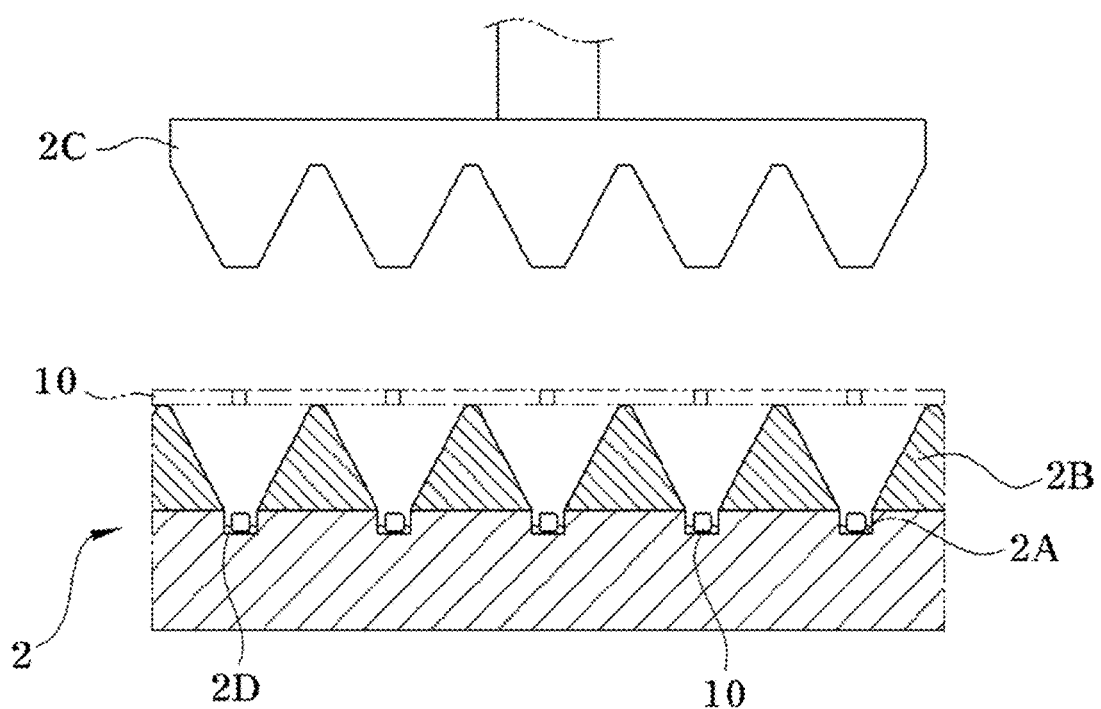
FIGS. 5a and 5b are configuration views illustrating an example in which the core material is inserted into a mold for manufacturing the structure to mold the structure according to the present invention.
Figure 5B:
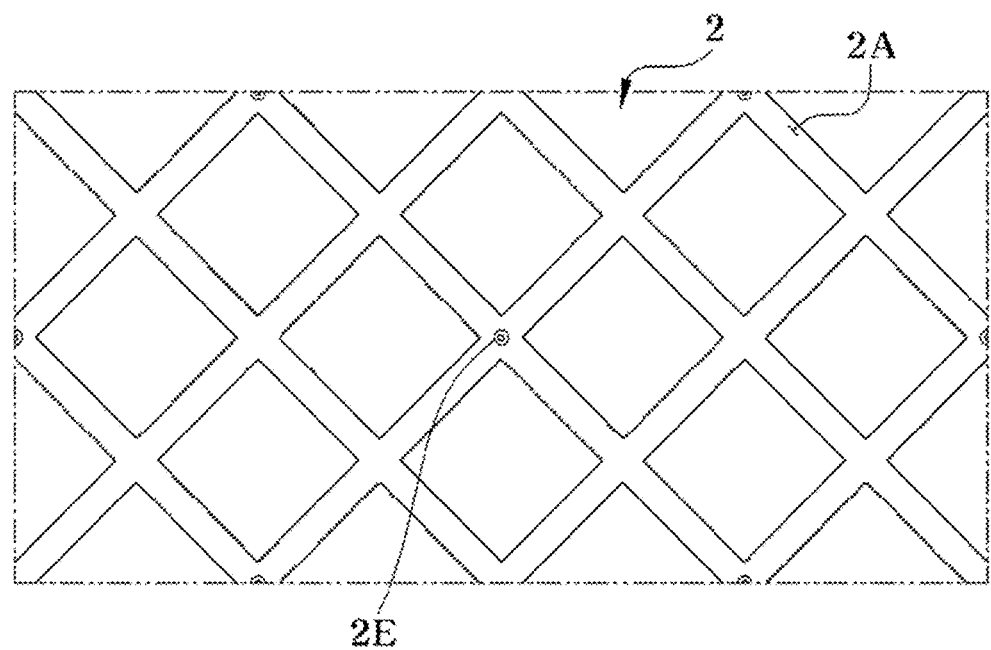

In this operation, the core material 10 is seated inside the mold 2 for manufacturing a structure so that the structure 20 is molded and attached to the outer circumferential surface of the core material 10 by the structure molding operation S300. To this end, the present invention includes a guide cap 2B which has a curved portion or an inclined portion at an upper portion thereof while having a net shape, as illustrated in FIGS. 5a and 5b, and is located above the mold 2 for manufacturing a structure, and a pressing member 2C which serves to push the core material 10 into the mold 2 for manufacturing a structure. Through such a configuration, first, when the core material 10 is put on the guide cap 2B and then the pressing member 2C is moved down toward the mold 2 for manufacturing a structure, the core material 10 put on the guide cap 2B may be moved down while being slid along the curved portion or the inclined portion of the guide cap 2B and may be easily seated inside the mold 2 for manufacturing a structure. Accordingly, the structure 20 may be uniformly attached to the outside of the core material 10, and also the mass production may be enabled.

Meanwhile, in this process, if the core material 10 is not located at a center of a groove 2A formed at the mold 2 for manufacturing a structure but is located to be leaned toward one side or a bottom of the mold 2 for manufacturing a structure when being inserted and seated into the mold 2 for manufacturing a structure, the structure 20 formed at the outer circumferential surface of the core material 10 may not be formed to have a predetermined thickness or more. Therefore, in the present invention, as illustrated in FIGS. 5a and 5b, to prevent this phenomenon, a protrusion-shaped spacer 2D may be selectively formed along a length at both sides of a bottom of the groove 2A of the mold 2 for manufacturing a structure in which the core material 10 is seated. Therefore, when the core material 10 is seated in the groove 2A of the mold 2 for manufacturing a structure, it may be located at the center thereof.

In addition to the above-described configuration, in the present invention, one or more protrusions 2E are formed at the mold 2 for manufacturing a structure to form a groove 21, in which a movable insertion spacer 3B is inserted, at a part of a lower surface of the structure 20.

Meanwhile, a structure and an operation of the movable insertion spacer 3B will be described later.

(3) Structure Molding Operation (S300)

In this operation, the structure 20 formed of the polycaprolactone composite material is molded at the outer circumferential surface of the core material 10 to cover the core material 10 after the core material 10 is seated inside the mold 2 for manufacturing a structure by the core material seating operation S200. In the previous operation, while the core material 10 is seated to be located at the center of the groove 2A of the mold 2 for manufacturing a structure, the polycaprolactone composite material including polycaprolactone as the main material is injected (insert-injected) into a space between the outside of the core material 10 and the groove 2A of the mold 2 for manufacturing a structure, and thus the structure 20 of the polycaprolactone composite material is molded to surround the outer circumferential surface of the core material 10.

At this point, in the structure 20, as described above, polycaprolactone is used as the main material, and the reinforcing agent formed of the fiber-reinforced glass fiber, carbon fiber, the polyethylene terephthalate fiber or the like is mixed with the main material which is polycaprolactone, and PE, PU or PB may also be added to control the time for applying the cast and also to reduce the material cost.

And a nucleating agent such as talc, sorbitol and sodium benzoate may be added to the polycaprolactone composite material forming the structure 20. Due to such an addition of the nucleating agent, the crystallization of the polycaprolactone composite material may be promoted, and thus the polycaprolactone composite material may be solidified within a short time. Accordingly, an injection molding time may be reduced, and productivity may be enhanced, and crystals of the polycaprolactone composite material may also be prevented from being excessively grown, and thus a uniform strength may be expected.

The structure 20 attached to and formed at the outer circumferential surface of the core material 10 by the insert injection is formed to have the quadrangular cross section shape in which the height thereof is relatively larger than the width thereof to ensure the sufficient rigidity with respect to the external force or the impact. At this point, the width of the structure 20 is 4 to 5 mm and the height thereof is 5.5 to 6.5 mm.

Also, when the cast is applied to the patient's affected part, a part (e.g. an elbow) at which the net-shaped cast is relatively greatly deformed in comparison with other part may be generated according to the body part at which the cast is applied. In this case, a flat surface of a portion thereof at which the structures 20 cross each other may not be maintained and thus the portion may protrude upward or downward based on the flat surface. At this point, when the structure 20 protrudes downward, a protruding portion may press the patient's skin, and thus the patient may feel uncomfortable.

Therefore, in the present invention, to prevent this phenomenon, a groove (not shown) which is recessed inward may be formed at the portion at which the structures 20 cross each other when the structure 20 is molded. Alternatively, a thickness of the portion at which structures 20 cross each other may be formed to be relatively thinner than another portion therearound. At this point, the recessed groove may be formed by forming a protruding portion (not shown) at the mold 2 for manufacturing a structure which molds the structure 20, and a configuration which allows the thickness of the portion, at which the structures 20 cross each other, to be relatively thinner may be achieved by forming a portion of the mold 2 for manufacturing a structure, which forms the portion, to be relatively thick.

In the present invention, since the structure 20 is manufactured by the insert injection using the mold 2 for manufacturing a structure, the structure 20 may be molded uniformly and rapidly, and it is advantageous in the mass production. Also, since a surface of the cast 1 is formed of the smooth structure 20, the patient does not feel uncomfortable even when the cast is in contact with the patient's skin.

(4) Outer Cover Molding Operation (S400)

In this operation, the outer cover 30 is molded at an outside of the structure 20. This operation is selectively performed as necessary.

When the structure molding operation S400 is performed, the cast 1 having the smooth surface is manufactured, and thus the patient does not feel uncomfortable even when the surface of the cast is in contact with the patient's skin. However, when the cast is cooled after being applied to the patient's affected part, the structure 20 becomes hard, and thus patient may feel uncomfortable. Therefore, in this present invention, the outer cover 30 formed of the rubber material is additionally formed at the outer circumferential surface of the structure 20, and thus the user does not feel uncomfortable when wearing the cast.

Figure 6:
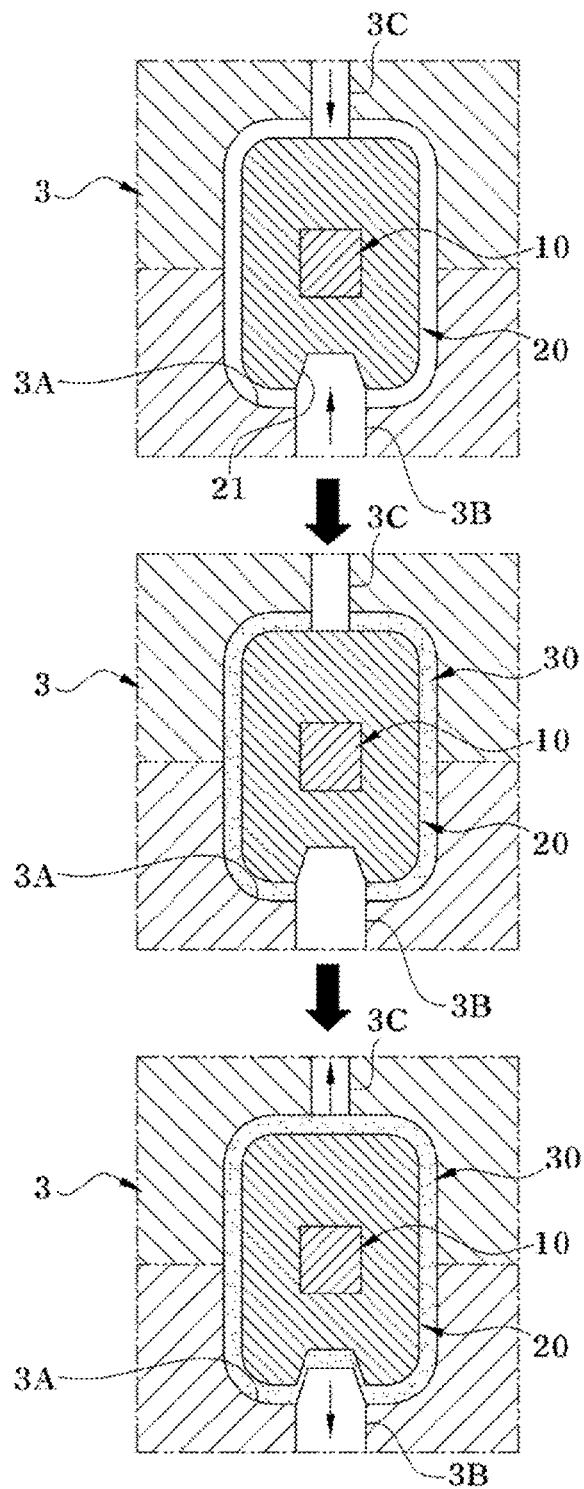
FIG. 6 is a configuration view illustrating an example in which an outer cover is molded at an outer circumferential surface of the structure according to the present invention.

As illustrated in FIG. 6, when the outer cover 30 is molded at the outer circumferential surface of the structure 20, the outer cover 30 is molded by injecting the rubber material for forming the outer cover 30 into a space between the structure 20 and the a molding groove 3A of a mold 3 for manufacturing an outer cover while the structure 20 is inserted into the mold 3 for manufacturing an outer cover, like the molding of the structure 20.

At this point, when the structure 20 is seated in the molding groove 3A of the mold 3 for manufacturing an outer cover, the structure 20 is adapted to be located at a center thereof, and thus when the outer cover 30 is molded, the outer cover 30 may have a predetermined thickness or more. To this end, as described above, one or more grooves 21 each of which has an inclined surface are distributed at a part of the lower surface of the structure 20, and the movable insertion spacer 3B which is formed to have a shape corresponding to the lower groove 21 of the structure 20 and a movable support spacer 3C which is installed in an opposite direction to the movable insertion spacer 3B are provided at the molding groove 3A of the mold 3 for manufacturing an outer cover.

A thickness of a lower surface of the outer cover 30 is formed thicker than that of each of both side surfaces and an upper surface thereof. The reason why the thickness of the lower surface is formed thicker than that of other portion is to allow the lower surface of the structure 20 to serve as a buffer material when being in contact with the patient's skin.

Due to such a configuration, when the outer cover 30 is molded, first, as illustrated in FIG. 6, the structure 20 in which the grooves 21 are distributed at the lower surface is seated in the molding groove 3A inside the mold 3 for manufacturing an outer cover, and the movable insertion spacer 3B and the movable support spacer 3C are simultaneously moved toward the structure 20, and thus the structure 20 is seated to be located at the internal center of the mold 3 for manufacturing an outer cover by the movable insertion spacer 3B and the movable support spacer 3C.

Figure 8A:
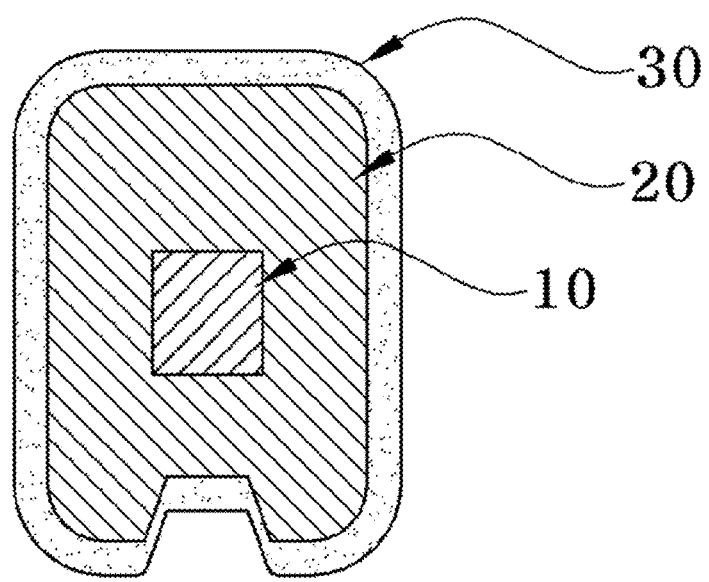
FIGS. 8a and 8b are cross-sectional views illustrating an example of the thermoplastic cast according to the present invention.

In this process, the movable insertion spacer 3B is guided by the inclined surface of the groove 21 formed at the lower surface of the structure 20 and inserted into the groove 21. In this state, the material of the outer cover 30 is injected to the space between the mold 3 for manufacturing an outer cover and the structure 20. At this point, when each of the movable insertion spacer 3B and the movable support spacer 3C formed at upper and lower surfaces thereof is moved backward from the structure 20 to an outside during a pressure holding process immediately after the injection, the outer cover 30 having the predetermined thickness or more is molded as illustrated in FIG. 8a.

Figure 7:
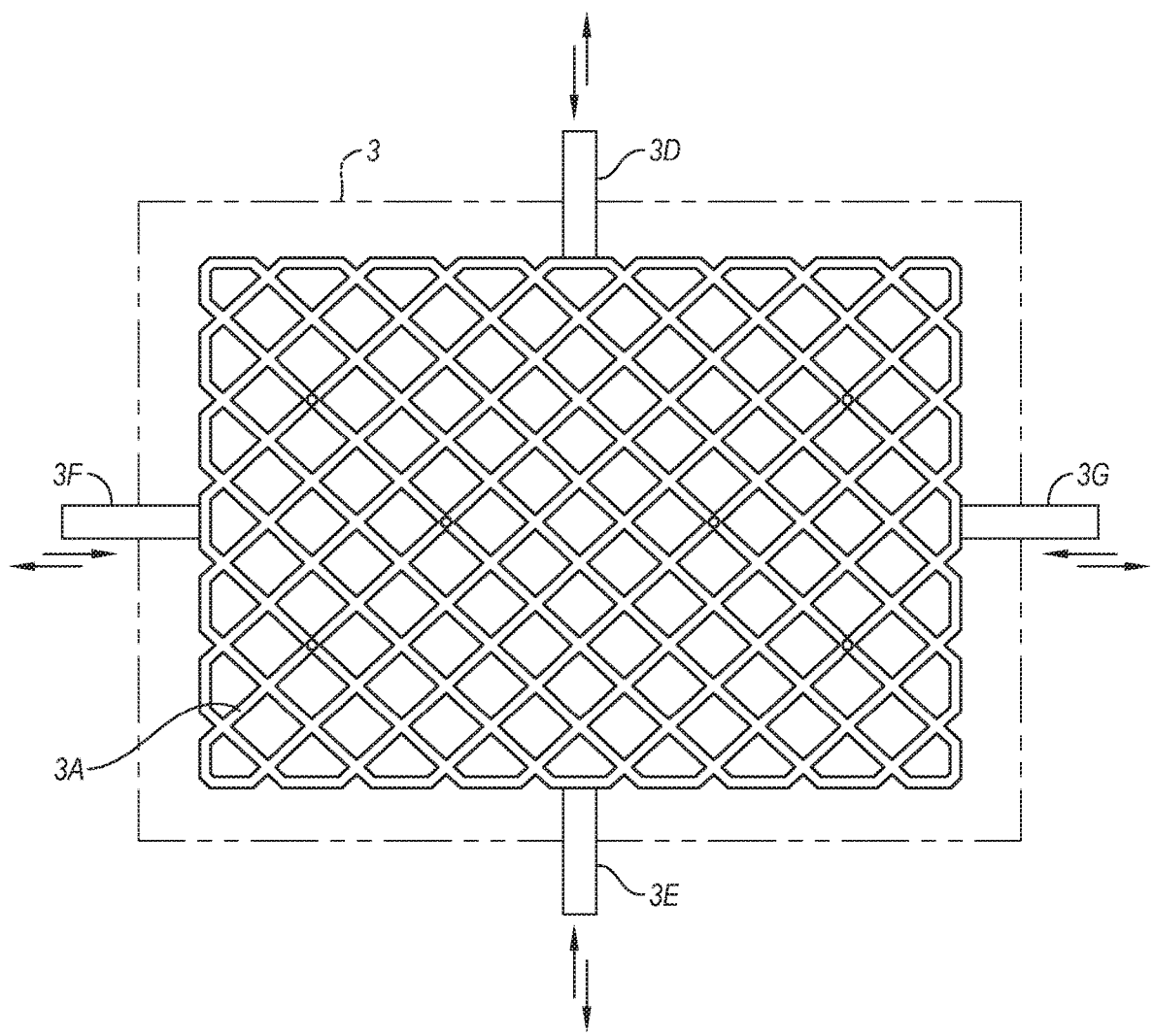
FIG. 7 is a configuration view illustrating an example of the mold for manufacturing the outer cover according to the present invention.
Figure 8B:
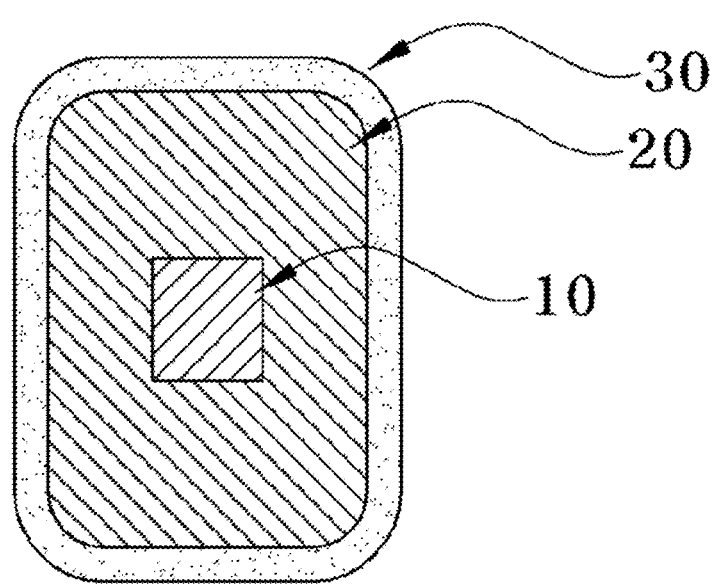

Meanwhile, the above description has described that the movable insertion spacer 3B and the movable support spacer 3C are provided at the upper and lower surfaces of the molding groove 3A of the mold 3 for manufacturing an outer cover and guided by the molding groove 3A formed at a lower portion of the structure 20 and then located at the center of the molding groove 3A. On the other hand, as illustrated in FIG. 7, in the mold 3 for manufacturing an outer cover, movable support spacers 3D, 3E, 3F and 3G may be provided at four side surfaces thereof located at the outermost side thereof, respectively. Each of the movable support spacers 3D, 3E, 3F and 3G may support an outer surface of the structure 20 which is located at the outermost side thereof so that the structure 20 is located at the center of the molding groove 3A. In this case, first, the structure 20 is seated in the molding groove 3A of the mold 3 for manufacturing an outer cover, and then the movable support spacers 3D, 3E, 3F and 3G protrude toward the molding groove 3A so that the four side surfaces of the structure 20 are guided by the movable support spacers 3D, 3E, 3F and 3G which are located at corresponding positions, respectively, and the structure 20 is located at the center of the molding groove 3A. Then, when the movable support spacers 3D, 3E, 3F and 3G are simultaneously moved backward while the material of the outer cover is injected into the space between the mold 3 for manufacturing an outer cover and the structure 20, the outer cover 30 having the predetermined thickness is molded at the outer circumferential surface of the structure 20, as illustrated in FIG. 8b.

As described above, since the cast 1 of the present invention is molded so that the outer cover 30 of the rubber material is formed at the outer circumferential surface of the structure 20 to have the predetermined thickness or more, the outer cover 30 may serve as the buffer material. Accordingly, even when the cast 1 is in direct contact with the patient's skin, the pressing to the skin is reduced, and thus a pain due to the pressing of the cast may be prevented. As a result, it is not necessary to separately install an underlying padding (a skin protection pad) or the like at the lower portion of the cast 1.

Figure 9:
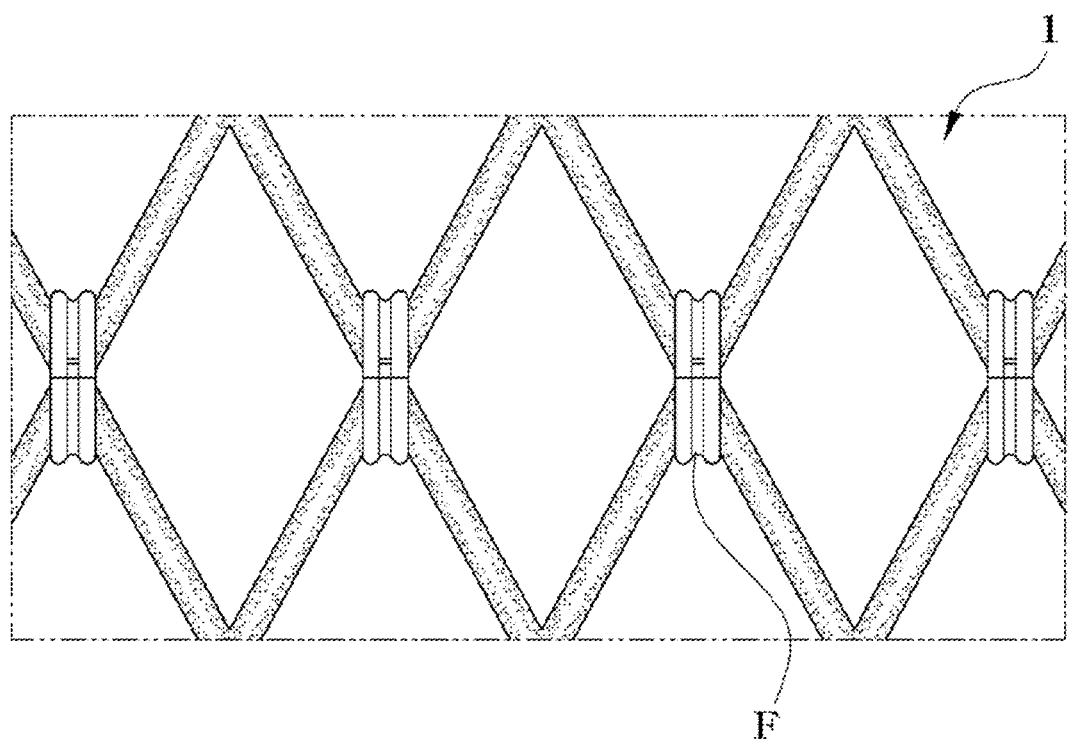
FIGS. 9 and 10 are a use state view and a photograph illustrating an example in which the cast according to the present invention is used while being fixed by a fixing member.
Figure 10:
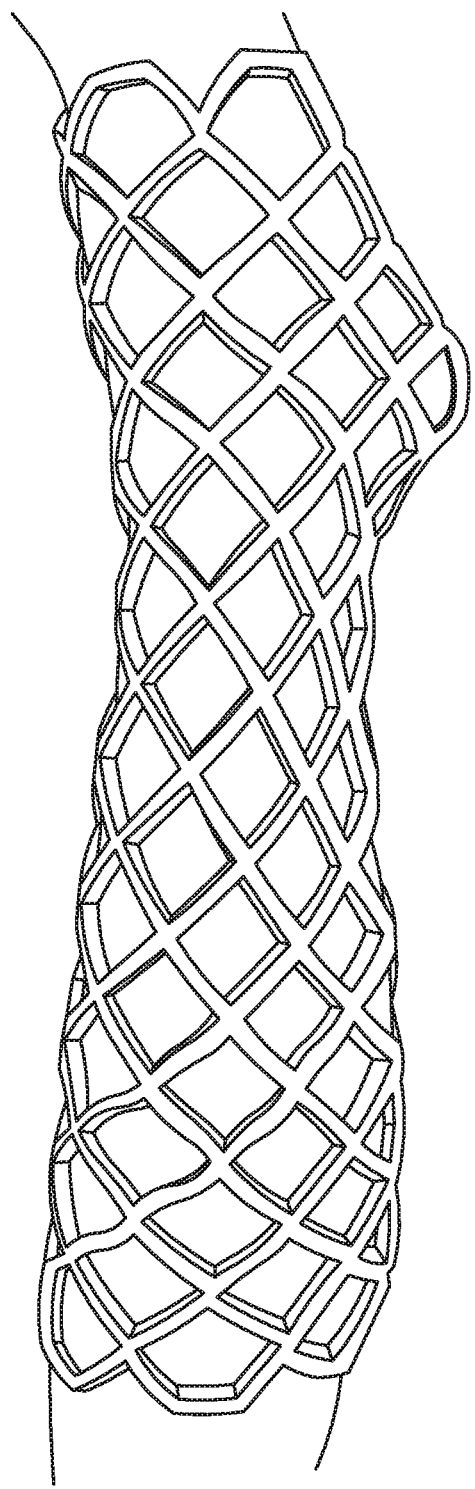

When the cast 1 of the present invention having the above-described configuration is applied to the patient's affected part, first, the cast 1 at a room temperature is heated by a heater such as an electronic range and a water bath to be softened and thus to be freely deformable and then applied to cover the patient's affected part which is fractured or needed to be corrected. Then, as illustrated in FIGS. 9 and 10, the cast 1 is slowly cooled to a room temperature and solidified while both ends thereof which are in contact with each other are fixed using a fixing member F, and then the both ends are connected by a fixing clip. Therefore, the application of the cast 1 is completed.

At this point, the fixing member F which is used to fix the both ends of the cast 1 may include a clip type or a buckle type and may have any configurations for fixing the both ends of the cast 1. However, the cast 1 may be formed of a plastic material rather than a metallic material so that a patient is allowed to perform an X-ray examination even while the patient wears the cast 1.

And when it is necessary to remove the cast 1 from the patient's affected part or to modify the cast 1, the fixing member F installed at both ends of the cast 1 is removed, and then the cast 1 may be removed by just slightly spreading the both ends of the cast 1, and thus removing thereof may be relatively easily performed. Then, when it is intended that the cast 1 is applied again to the patient's affected part, the removed cast 1 may be heated again to be softened and then may be easily modified and applied again through the above-described application process of the cast 1.

As described above, as the cast according to the present invention is formed in the net shape, breathability is improved, and also as the structure formed of the polycaprolactone composite material is formed to surround outside the core material by insert injection, the structure is structurally rigid and does not cause the patient to feel uncomfortable, and since the structure is formed of a thermoplastic material, it can be modified and used again by heating as necessary. Although a few embodiments of the present invention have been shown and described, it would be appreciated by those skilled in the art that changes may be made in these embodiments without departing from the principles and spirit of the invention, the scope of which is defined in the claims and their equivalents.

INDUSTRIAL APPLICABILITY

The invention claimed is:

1. A thermoplastic cast configured to cover and fix a fractured part of a patient's body, comprising:
    a structure configured to cover at least a part of the fractured part of the patient; and
    an outer cover that covers the structure;
    wherein the structure includes a thermoplastic resin configured to be deformed to conform to the part of the fractured part by heating,
    wherein the structure is formed as a net shaped body with holes,
    wherein the structure and the outer cover are configured to be deformed to conform to the part of the fractured part thanks to the holes,
    wherein the thermoplastic cast comprises a plurality of elongate portions connected together and crossing each other,
    wherein a cross-section of each of the plurality of elongate portions in a plane orthogonal to a length of the corresponding elongate portion comprises the structure surrounded by the outer cover,
    wherein a first elongate portion of the plurality of elongate portions includes a groove that is recessed inward in a first direction orthogonal to a length of the first elongate portion,
    wherein in a cross-section of the first elongate portion in a plane orthogonal to a length of the first elongate portion and that passes through the groove, a thickness of the first elongate portion is thinner at the groove than to either side of the groove;
    wherein the groove is recessed inward in the first elongate portion at an intersection of the first elongate portion with a second elongate portion of the plurality of elongate portions of the structure; and
    wherein the plurality of elongate portions make up the net shaped body, each of the plurality of elongate portions individually being devoid of the holes of the net shaped body along its respective length.

2. The thermoplastic cast of claim 1, wherein the groove has an inclined surface.

3. The thermoplastic cast of claim 1, the thermoplastic cast further comprising:
    a core material having a net shape by molding a synthetic resin elastomer into the net shape by injection molding or press-working;
    wherein the structure surrounds the core material.

4. The thermoplastic cast of claim 3, wherein the core material has a first melting point and the structure has a second melting point that is lower than the first melting point of the core material.

5. The thermoplastic cast of claim 3, wherein each of the core material and the outer cover comprises an elastic material.

6. The thermoplastic cast of claim 1, wherein the structure includes a polycaprolactone composite.

7. The thermoplastic cast of claim 6, wherein fiber-reinforced glass fiber, carbon fiber or a polyethylene terephthalate fiber is added to the polycaprolactone composite.

8. The thermoplastic cast of claim 6, wherein polyethylene (PE), polyurethane (PU) or polybutene (PB) is added to the polycaprolactone composite.

9. The thermoplastic cast of claim 6, wherein one of talc, sorbitol and sodium benzoate as a nucleating agent is added to the polycaprolactone composite.

10. The thermoplastic cast of claim 1, wherein the outer cover is formed to cover the structure by insert injection.

11. The thermoplastic cast of claim 1, wherein the cross-section of each of the plurality of elongate portions in the plane orthogonal to the length of the corresponding elongate portion is quadrangular with a height that is greater than a width of the cross-section.

12. A thermoplastic cast configured to cover and fix a fractured part of a patient's body, comprising:
    a net-shaped reticulate body comprising a plurality of elongate portions, wherein:
        the plurality of elongate portions includes a first subset of elongate portions and a second subset of elongate portions;
        the first subset of elongate portions are arranged parallel to each other;
        the second subset of elongate portions are arranged parallel to each other;
        the first subset of elongate portions are not parallel to the second subset of elongate portions;
        each of the first subset of elongate portions intersects some of the second subset of elongate portions;
        each of the second subset of elongate portions intersects some of the first subset of elongate portions;
        each of the plurality of elongate portions includes a cross-section orthogonal to a length of a corresponding elongate portion that includes a core surrounded by an intermediate layer and the intermediate layer surrounded by an outer cover;
        a specific elongate portion of the plurality of elongate portions includes a recess that extends from a bottom of the specific elongate portion inward toward the core;
    in a cross-section of the specific elongate portion orthogonal to the length of the specific elongate portion and through the recess, the cross-section of the specific elongate portion:
        has a first thickness at the recess through the outer cover, the intermediate layer, and the core; and
        has a second thickness to either side of the recess exclusively through the outer cover and the intermediate layer; and
    the first thickness at the recess through the outer cover, the intermediate layer, and the core is less than the second thickness to either side of the recess exclusively through the outer cover and the intermediate layer.

13. The thermoplastic cast of claim 12, wherein the core comprises a first material with a first melting point and the intermediate layer comprises a second material with a second melting point that is lower than the first melting point.

14. The thermoplastic cast of claim 12, wherein:
    each of the core and the outer cover comprises an elastic material; and
    the intermediate layer comprises a thermoplastic resin.

15. The thermoplastic cast of claim 12, wherein:
    the core comprises a synthetic resin elastomer; and
    the intermediate layer comprises a polycaprolactone composite.

16. The thermoplastic cast of claim 12, wherein the cross-section of each of the plurality of elongate portions orthogonal to the length of the corresponding elongate portion is quadrangular with a height that is greater than a width of the cross-section.

17. The thermoplastic cast of claim 12, wherein the recess is formed at an intersection of the specific elongate portion with an other elongate portion, the specific elongate portion included in the first subset of elongate portions and the other elongate portion included in the second subset of elongate portions.

\* \* \* \* \*